(12) United States Patent
LaBombard

(10) Patent No.: US 8,920,311 B2
(45) Date of Patent: Dec. 30, 2014

(54) ADAPTER FOR ATTACHING DEVICES TO ENDOSCOPES

(75) Inventor: Denis LaBombard, Georgetown, MA (US)

(73) Assignee: Aponos Medical Corp., Kingston, NH (US)

( * ) Notice: Subject to any disclaimer, the term of this patent is extended or adjusted under 35 U.S.C. 154(b) by 732 days.

(21) Appl. No.: 12/592,003

(22) Filed: Nov. 18, 2009

(65) Prior Publication Data

US 2010/0125164 A1    May 20, 2010

Related U.S. Application Data

(60) Provisional application No. 61/199,606, filed on Nov. 18, 2008, provisional application No. 61/268,813, filed on Jun. 17, 2009.

(51) Int. Cl.
*A61B 1/04* (2006.01)
*A61B 1/00* (2006.01)
*A61B 17/064* (2006.01)
*A61B 5/00* (2006.01)
*A61B 17/00* (2006.01)

(52) U.S. Cl.
CPC ......... *A61B 1/00087* (2013.01); *A61B 17/0644* (2013.01); *A61B 2017/0641* (2013.01);
(Continued)

(58) Field of Classification Search
CPC ........... A61B 1/00064; A61B 1/00071; A61B 1/0008; A61B 1/00089; A61B 1/00101
USPC .................................. 600/104, 121-125, 127
See application file for complete search history.

(56) References Cited

U.S. PATENT DOCUMENTS 3,266,059 A    8/1966  Stelle
5,201,908 A *  4/1993  Jones ............................. 600/123
(Continued)

FOREIGN PATENT DOCUMENTS

DE        197 11 673 A1   10/1998
DE    10 2004 015291 A1   10/2004
(Continued)

OTHER PUBLICATIONS

International Search Report in International Application No. PCT/US2009/006164, 5 pages, mailed Mar. 5, 2010.

(Continued)

*Primary Examiner* — Matthew J Kasztejna
(74) *Attorney, Agent, or Firm* — Hamilton, Brook, Smith & Reynolds, P.C.

(57) ABSTRACT

An improved system for attaching devices to the distal end of endoscopic instruments is described. An attachment adapter comprises a distal stop, such as a complete or partial loop or cylinder, which limits the penetration of an endoscope into the adapter. The adapter has at least one flange protruding proximally along the endoscope. The adapter is secured on the endoscope by a securing means, which compresses the flange or flanges sufficiently to provide a friction fit. The flexibility of the inventive adapter system allows the adapter to work reliably with endoscopes that are used, damaged or repaired. The adapter may further provide a slit or window allowing viewing of the vessel wall by a lens on an endoscope, thereby improving the operator's ability to understand the location of the endoscope during operation. The adapter may carry any of a variety of devices, including devices for closing a surgical incision, or treating or manipulating tissue. Improvements are described in a number of areas to allow more flexible pairing of particular endoscopes or endoscopic instruments with devices to be carried on their exteriors, while maintaining a tightly locked position of the external device on the carrier.

26 Claims, 7 Drawing Sheets

(52) U.S. Cl.
CPC ........... *A61B 5/4839* (2013.01); *A61B 1/00101* (2013.01); *A61B 2017/00473* (2013.01); *A61B 1/00089* (2013.01); *A61B 2017/0645* (2013.01); *A61B 1/0014* (2013.01); *A61B 2017/00296* (2013.01); *A61B 1/00128* (2013.01); *A16B 17/068* (2013.01); *A61B 1/00142* (2013.01); *A61B 17/0057* (2013.01); *A61B 2017/00668* (2013.01)
USPC ........... 600/127; 600/104; 600/121; 600/123; 600/124; 600/125

(56) References Cited

U.S. PATENT DOCUMENTS

| | | | | |
|---|---|---|---|---|
| 5,217,001 | A * | 6/1993 | Nakao et al. | 600/123 |
| 5,381,782 | A | 1/1995 | DeLaRama et al. | |
| 5,386,817 | A * | 2/1995 | Jones | 600/104 |
| 5,972,002 | A | 10/1999 | Bark et al. | |
| 6,059,719 | A * | 5/2000 | Yamamoto et al. | 600/127 |
| 6,071,233 | A * | 6/2000 | Ishikawa et al. | 600/104 |
| 6,152,937 | A | 11/2000 | Peterson et al. | |
| 6,196,966 | B1 * | 3/2001 | Kerin et al. | 600/104 |
| 6,197,042 | B1 | 3/2001 | Ginn et al. | |
| 6,293,909 | B1 * | 9/2001 | Chu et al. | 600/121 |
| 6,306,081 | B1 * | 10/2001 | Ishikawa et al. | 600/127 |
| 6,428,548 | B1 | 8/2002 | Durgin et al. | |
| 6,450,948 | B1 | 9/2002 | Matsuura et al. | |
| 6,520,974 | B2 | 2/2003 | Tanner et al. | |
| 6,569,085 | B2 * | 5/2003 | Kortenbach et al. | 600/104 |
| 6,582,452 | B2 | 6/2003 | Coleman et al. | |
| 6,602,263 | B1 | 8/2003 | Swanson et al. | |
| 6,669,708 | B1 | 12/2003 | Kim et al. | |
| 6,699,180 | B2 * | 3/2004 | Kobayashi | 600/127 |
| 6,726,704 | B1 | 4/2004 | Loshakove et al. | |
| 6,849,078 | B2 | 2/2005 | Durgin et al. | |
| 6,911,032 | B2 | 6/2005 | Jugenheimer et al. | |
| 6,926,731 | B2 | 8/2005 | Coleman et al. | |
| 6,974,411 | B2 | 12/2005 | Belson | |
| 7,001,398 | B2 | 2/2006 | Carley et al. | |
| 7,056,284 | B2 * | 6/2006 | Martone et al. | 600/123 |
| 7,059,508 | B2 | 6/2006 | Shelton, IV et al. | |
| 7,189,247 | B1 | 3/2007 | Zirps et al. | |
| 7,204,804 | B2 | 4/2007 | Zirps et al. | |
| 7,575,548 | B2 * | 8/2009 | Takemoto et al. | 600/104 |
| 7,588,580 | B2 * | 9/2009 | Okada | 606/113 |
| 8,182,422 | B2 * | 5/2012 | Bayer et al. | 600/175 |
| 8,313,496 | B2 * | 11/2012 | Sauer et al. | 606/139 |
| 2001/0053909 | A1 | 12/2001 | Nakada et al. | |
| 2002/0055668 | A1 | 5/2002 | Pauker | |
| 2002/0082641 | A1 | 6/2002 | Ginn et al. | |
| 2002/0133150 | A1 | 9/2002 | Whayne | |
| 2002/0188318 | A1 | 12/2002 | Carley et al. | |
| 2003/0153932 | A1 | 8/2003 | Spence | |
| 2003/0158578 | A1 | 8/2003 | Pantages et al. | |
| 2004/0087981 | A1 | 5/2004 | Berube et al. | |
| 2004/0097982 | A1 | 5/2004 | Jugenheimer et al. | |
| 2004/0210111 | A1 | 10/2004 | Okada | |
| 2004/0230095 | A1 * | 11/2004 | Stefanchik et al. | 600/104 |
| 2005/0075538 | A1 | 4/2005 | Banik et al. | |
| 2005/0107667 | A1 | 5/2005 | Danitz et al. | |
| 2005/0283188 | A1 | 12/2005 | Loshakove et al. | |
| 2006/0058582 | A1 | 3/2006 | Maahs et al. | |
| 2006/0069304 | A1 * | 3/2006 | Takemoto et al. | 600/104 |
| 2006/0135989 | A1 | 6/2006 | Carley et al. | |
| 2007/0197862 | A1 * | 8/2007 | Deviere et al. | 600/102 |
| 2007/0225762 | A1 | 9/2007 | LaBombard | |
| 2007/0270752 | A1 | 11/2007 | LaBombard | |
| 2010/0038403 | A1 | 2/2010 | D'Arcangelo | |
| 2010/0048988 | A1 | 2/2010 | Pastorelli et al. | |
| 2010/0069933 | A1 | 3/2010 | D'Arcangelo et al. | |
| 2010/0133320 | A1 | 6/2010 | Bilotti et al. | |

FOREIGN PATENT DOCUMENTS

| | | |
|---|---|---|
| WO | WO 03/071955 | 9/2003 |
| WO | WO 2004/103430 A2 | 12/2004 |
| WO | WO 2010/059200 A1 | 5/2010 |

OTHER PUBLICATIONS

International Preliminary Report on Patentability in International Application No. PCT PCT/US2009/006164, 13 pages, mailed May 24, 2011.

Guarner-Argente, C., et al., "Yes, we can: reliable colonic closure with the Padlock-G clip in a survival porcine study (with video)", *Gastrointestinal Endoscopy*, 72(4):841-844 (2010).

Desilets, D., et al., "Gastric closure in NOTES using a novel, over-the-scope nitinol clip—A survival study in an animal model", International NOSCAR Conference on NOTES (4th). Boston, MA. Jul. 9-Jul. 11, 2009, 1 page.

Desilets, D., et al., "Gastrotomy closure with the lock-it system and the Padlock-G clip: a survival study in a porcine model", *J. Laparoendosc. Adv. Surg. Tech. A.*, 20(8):671-676 (2010). PubMed Abstract, available at: http://www.ncbi.nlm.nih.gov/pubmed/20687850, 1 page.

Romanelli, J.R., et al., "Natural orifice transluminal endoscopic surgery gastrotomy closure in porcine explants with the Padlock-G clip using the Lock-It system", *Endoscopy*, 42:306-310 (2010).

International Search Report and Written Opinion, PCT/US2007/007396, entitled "Self Closing Tissue Fastener," mailed Aug. 30, 3007.

International Search Report from International Application No. PCT/US2007/012049, entitled "Multifunctional Instrument Introducer," mailed Nov. 6, 2007.

Written Opinion of the International Searching Authority from International Application No. PCT/US2007/012049, entitled "Multifunctional Instrument Introducer," mailed Nov. 6, 2007.

Cotton, P. B., "Interventional Gastroenterology (Endoscopy) at the Crossroads: A Plea for Restructuring in Digestive Diseases," *Gastroenterology*, 107:294-299 (1994).

Fritscher-Ravens, A., et al., "Transgastric Gastropexy and Hiatal Hernia Repair for GERD Under EUS Control: A Porcine Model," *Gastrointest Endosc*, 59(1):89-95 (2004).

Jagannath, S. B. et al., "Peroral Transgastric Endoscopic Ligation of Fallopian Tubes with Long-Term Survival in a Procine Model," *Gastrointest Endos*, 61(3):449-453 (2005).

Modlin, I. M., "Perspectives and Reflections on Integrated Digestive Surgery," *Best Practice & Res Clin Gastroenterol*, 16(6):885-914 (2002).

Ponsky, J. L., Gastroenterologists as Surgeons "What They Need to Know", *Gastrointest Endosc*, 61(3):454 (2005).

ASGE/SAGES Working Group on Natural Orifice Translumenal Endoscopic Surgery, *Gastrointest Endosc*, 63(2):199-203 (2006).

Vitale, G. C., et al., "The Advancing Art and Science of Endoscopy", *Amer J. Surg*, 190:228-233 (2005).

\* cited by examiner

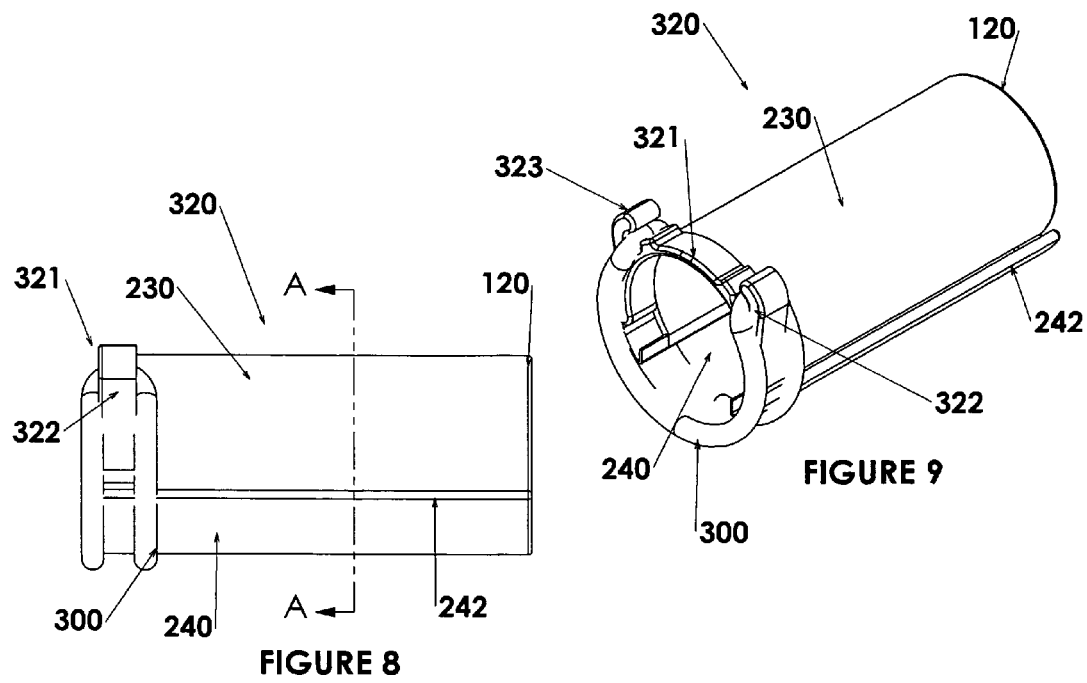
FIGURE 8
FIGURE 9
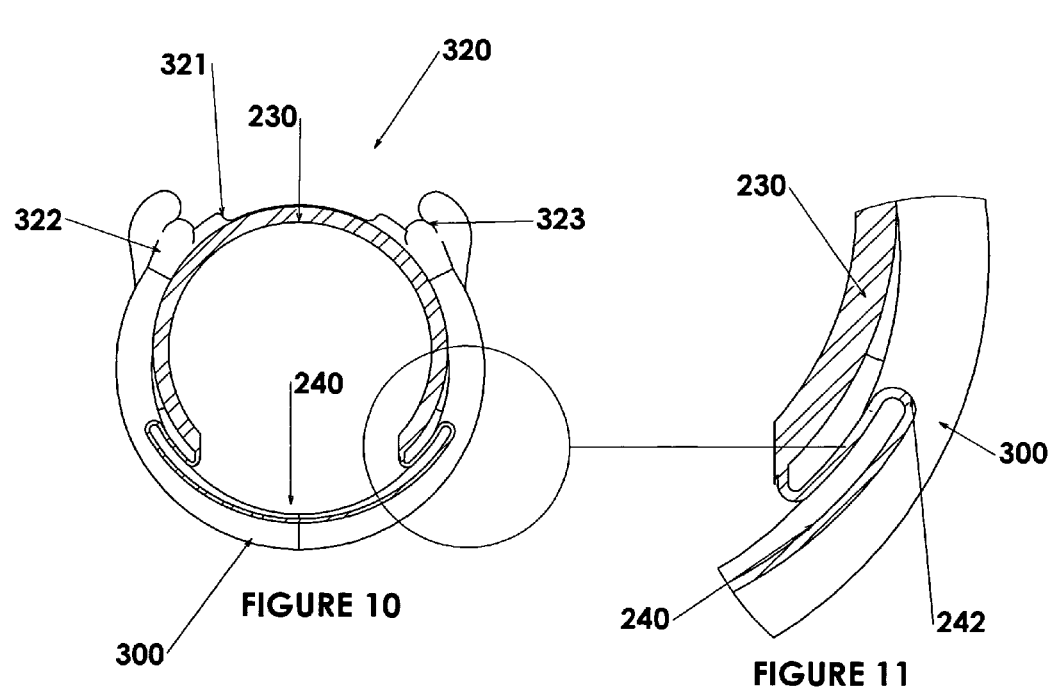
FIGURE 10
FIGURE 11

ADAPTER FOR ATTACHING DEVICES TO ENDOSCOPES

This application claims the benefit of the priority of U.S. provisional application 61/199,606, filed Nov. 18, 2008, and 61/268,813, filed Jun. 17, 2009. These applications are incorporated herein by reference in their entirety, where such incorporation is permitted.

BACKGROUND

Flexible endoscopes are axially elongate instruments that are navigable through natural body lumens of a patient for remotely evaluating and/or treating a variety of ailments. Endoscopes have viewing capability provided by fiber optic elements that transmit images along their length to the medical care provider. Endoscopes may be specifically configured in length, diameter, flexibility and lumen configuration to navigate to specific treatment areas in the body and conduct specific procedures. Such a specifically configured endoscope may be known by a specific or functional name, for example as a laparoscope, duodenoscope, colonoscope, sigmoidoscope, bronchoscope or urethroscope.

In combination with remote viewing capability, endoscopes are frequently configured to provide a working channel through which shaft mounted tools and medical instruments may be navigated and remotely operated. More recently, flexible endoscopes have also been used to deliver devices, medications or coatings to internal sites.

The outer diameter of flexible endoscopes varies depending on style and intended function. For example, a flexible endoscope typically used in gastric procedures, having a single instrument channel, can have a nominal diameter ranging from under 10 mm to over 12 mm (e.g., the Olympus XGIF-Q160Y9 single channel endoscope), while a dual instrument channel endoscope may range in diameter from under 12 mm to 15 mm or larger, (e.g. the Olympus GIF2T160). There is no absolute gauge or completely standard set of sizes in the industry at present. The particular endoscope for a given procedure is selected by the physician, and may vary depending on procedure and cost related factors. Hence, the geometric size of an instrument which may be used in a specific procedure is generally impossible to predict.

Moreover, endoscopes are typically constructed of wall-forming parts that are interconnecting but flexible, and a fluid-impermeable coating, typically of plastic reinforced with fabric. The resulting instruments are complex and expensive, and so they are normally re-used, after cleaning and sterilization. These procedures can alter the diameter, and especially the shape, of the instrument in general and especially of the distal tip zone, which is the area of highest articulation and wear.

To accommodate multiple functions within a single instrument construct, there are typically a number of different discrete functional elements bundled within the instrument. Such elements of a typical flexible endoscopic instrument include visualization systems, such as an optical fiber light source and a fiber bundle visualization system with a terminal lens; one or two passages for other functions, such as drug delivery or tissue manipulation; insufflation channels for injecting air or gasses into the body cavity; multiple control wires for distal tip articulation; and fluid channels to direct fluid across the visual imaging lens to remove to flush debrief or tissue which may occlude it. Endoscopic design is very configuration specific, for in order to accommodate these multiple functions in an articulating tip, an endoscope will typically need to have these features arrayed in a pattern which can be best visualized and understood by thinking of the endoscope as being composed of a number of wedges, like a sliced pizza, each with a different function, flowing axially.

As a result, most current endoscopes have their viewing optics, and often their illuminating optics, in an off-center location. Often, no one feature of a multifunctional flexible endoscopic instrument is located on the direct central axis of the instrument. In fact, it may be advantageous to not have any feature aligned with the instrument centerline of the distal tip feature, to allow stabilizing the device with a tension wire secured at the axis centerline to the distal end of the articulating portion. This feature location method is one effective way to apply a tension to lock together the various nesting or articulating elements of the endoscope, while still allowing multiple degrees of freedom to move a discrete distal portion of the device by use of control wires located in an axial array running along the outer circumference of the instrument. This layout of features is well known and documented in endoscope designs. In particular, as documented in many endoscopic products with off axis optics, and as generally represented by the Olympus XGIF-Q160Y9 and Olympus GIF2T160 instruments, an imaging lens at the distal tip of the flexible endoscopic instrument will usually not be positioned on the center axis of the instrument itself but rather located at an offset position with respect to the centerline of the instrument.

These geometries require adaptations to perform other functions of the endoscope, and in particular favor mounting components on the outside of the endoscope tip. For example, U.S. Pat. No. 7,204,804 to Zirps et al. describes a mounting adapter for releaseably securing accessories, tools, or medical instruments to the distal end of an endoscope. The adapter is most compatible with endoscopic accessories that have a cylindrical mounting surface, and is positioned over a length of the distal end of an endoscope. The Zirps et al adaptor is provided in two components to support both ends of a cylindrical accessory on the endoscope surface. This adapter holds the accessory on the endoscope shaft by frictional engagement, and is configured to maintain the accessory concentric with the shaft along its length. The adapter also is configured to mount an accessory on a wide range of commercially available endoscopes, and to do this, it requires a number of different and distinct sizes of adaptor, typically provided together in a kit, to cover a wide range of instrument size and variation. Even with multiple sizes of insert, the actual diameter adaptability has a narrow range—for example, a range of from 10 to 11.3 mm, with three different diameters of adapter, is cited.

This particular adapter is ideally most suited to securing an attachment to a smooth, cylindrically concentric endoscopic instrument (such as a rigid laparoscope with an imaging lens located centrally), because it uses a series of multiple compressing fingers radially emanating from an axially located and axially centered ring feature, and is secured by a second closed perimeter concentric locking collar. Such mechanisms are known in the art, and as commonly used in the machine tool industry are known as "collets". The holding system presented in the No. 7,204,804 Zirps et al patent is a collet type of holding system and is described in Wikipedia and other Machine Tool and Woodworking descriptive glossaries as follows:

"A collet is a holding device—specifically, a subtype of chuck—that forms a collar around the object to be held and exerts a strong clamping force on the object when it is tightened via a tapered outer collar. It may be used to hold a work piece or a tool. Generally, a collet chuck, considered as a unit, consists of a tapered receiving sleeve (often integral with the machine spindle), the collet proper (usually made of spring steel), which is inserted into the receiving sleeve, and (often) a cap that screws over the collet, clamping it via another taper."

Collet based systems require, by their design and function, the geometrical property that the centerline axes of "the machine spindle", "the collar around the object", "the outer collar" and "a work piece or a tool" as described in the above definition be co-axial. The use of a collet design requires that the article or tool grasping system typically be comprised of at least two or more finger-like entities arrayed as an even number of axial symmetric finger-like entities placed as matching pairs or an odd number of symmetric shaped finger like entities, evenly radially arrayed about a diameter which are then diametrically compressed in unison by a second cylindrical embodiment moving (slideably) in an axial direction to engage the article to be secured which in this art is an endoscope. Such uniform radial compressions systems using multiple finger-like gripping features are highly advantageous where the concentric, coaxial alignment of the engaging system and the article to be secured must be maintained (such as high speed spinning of a cutting tool in a hand drill or machine tool spindle for example). Similar features and attributes as described by No. 7,204,804 Zirps et al are used to align the axis of the article to be secured (the device attached to the 'collet' system of Zirps) with the central axis of the positioning instrument (the endoscope) thus providing coaxial positioning.

For the purposes of this application the geometric definition of a cylinder from the Encyclopedia Britannica is hereby cited (http://www.britannica.com/EBchecked/topic/148295/cylinder).

"In geometry, a surface of revolution that is traced by a straight line (the generatrix) that always moves parallel to itself or some fixed line or direction (the axis). The path, to be definite, is directed along a curve (the directrix), along which the line always glides. In a right circular cylinder, the directrix is a circle. The axis of this cylinder is a line through the centre of the circle, the line being perpendicular to the plane of the circle. In an oblique circular cylinder, the angle that the axis makes with the circle is other than 90°. The directrix of a cylinder need not be a circle, and if the cylinder is right, planes parallel to the plane of the directrix that intersect the cylinder produce intersections that take the shape of the directrix. For such a plane, if the directrix is an ellipse, the intersection is an ellipse. The generatrix of a cylinder is assumed to be infinite in length; the cylinder so generated, therefore, extends infinitely in both directions of its axis. A finite cylinder has a finite base, the surface enclosed by the directrix, and a finite length of generatrix, called an element."

A number of tissue-closing devices in the current art describe mounting and securing techniques for positioning of a securing device on an endoscope. Such embodiments typically use cap-like distal mounts and elastomeric securing rings. Examples include U.S. Pat. Nos. 5,320,630 and 5,462,559 to Ahmed, U.S. Pat. No. 5,697,940 to Chu et al., U.S. Pat. No. 5,853,416 to Tolkoff, U.S. Pat. No. 6,974,466 to Ahmed et al, U.S. Pat. No. 7,214,231 to Tolkoff and U.S. Pat. No. 7,189,247 Zirps et. al. These patents describe a class of ligator band products currently in the marketplace. These references also describe the design and application of various endoscope-based or endoscope-mounted delivery systems and means for securing them to the end of an endoscope. These delivery systems are used to locate and place a tissue-closing embodiment during a surgical procedure, and typically comprise an elastic annular loop or ring feature which grips the endoscopic instrument's outer diameter circumferentially at a location near its distal end, with the ring-like loop being coupled to a rigid cap-like member located distally of the endoscopic instrument distal end. These embodiments are mounted sealably on the endoscope tip, and held in place by the radial compressive force of the elastic member on the instrument gripping the endoscopic instrument with a uniform compressive force and providing general coaxial alignment. Such designs are well known in the art and typically create a central chamber distal to the endoscope tip inside the cap, such that vacuum energy applied through an instrument channel can draw tissue into the central chamber for the mounted device to secure.

Another type of tissue closing embodiment is exemplified by a serpentine closure device which is carried on the outside of the distal tip of a delivery tube (which may be an endoscope), and which is deployed by pushing the device off of the end of the tube. This type of tissue closing device delivered on the end of an endoscope is described by US patents to Durgin et al, including U.S. Pat. No. 6,428,548, U.S. Pat. No. 6,849,078, U.S. Pat. No. 7,211,101, U.S. Pat. No. 7,001,398 and US 2006/0135989. The placement device used in positioning this embodiment also has a cap mounted on the external end of the endoscopic instrument, functioning essentially as described above in band ligation technology.

Another type of device and its delivery are described in commonly-owned pending applications US 2007/0225762 and US 2007/0270752. These applications describe a tissue closure device comprising a superelastic torsion ring with stabilizing and tissue-piercing projections, which can be carried either on the inside or outside of an endoscope or tubular member, and a device for facilitating its delivery. Positioning on the inside of an endoscope distal end or introducer tube is preferred, and is advantageous to prevent interaction of the closure device with tissue during transport, site location and manipulation.

Figures and descriptions within the present application describe the integration of the commonly-owned pending application tissue closing device into the present invention with a specific and unique geometry to enable effective safe and secure delivery of tissue closing fasteners by an endoscopic instrument.

All described prior art embodiments known including the above described commonly-owned pending applications US 2007/0225762 and US 2007/0270752 and co-pending U.S. application No. 61/199,606 have followed the basic design principle of using a flexible, closed perimeter, generally cylindrical adapter to align concentric and co-axial the delivery device or attachment device center axis with the endoscopic instrument center axis, and then, in some cases, applying a component for providing some form of direct or indirect radial compression forces to effect a vacuum seal and a secure the device position. Such devices are portrayed as having a closed perimeter, i.e. a hollow cylinder forming by a complete circle. This art further describes a sealable chamber created by the coupling of the distal device carrier to the endoscopic instrument, which is located distal to the endoscopes' most distal feature, such that vacuum energy can be applied to draw tissue into the defined chamber. Alternatively, graspers or any type of tissue manipulation means may be employed to draw tissue in said chamber to effect a closure All of the instruments used in the above-cited art for locating and positioning the described devices can be described as "endoscopic instruments", and in this application, the word "endoscope" or "endoscopic" will refer to the entire class of endoscopic and laparoscopic instruments, including other surgical instruments intended to be used to remotely manipulate tissue in a surgical procedure, unless stated otherwise.

While it is feasible to design an externally-mounted device for a particular endoscope in its original condition, for example a 10 mm endoscope, it can be very difficult to use such a system on endoscopes which have repeatedly been resterilized or repaired. The distal end of such endoscopes can become somewhat non-circular with use, and the fabric-based outer sheath can loosen. As a result, it is hard to get an externally-mounted device to slide onto a used endoscope, and yet remain in a tightly locked state during the conduct of a medical procedure. Elastic mountings that are tight enough for new endoscopes may not fit onto old endoscopes, while mountings that will fit can be too loose for stable positioning during procedures. Even with an appropriate diameter, the externally-mounted device may rock or tilt when being inserted or removed, and there is a risk of detachment of the device from the endoscope while in the body. While in principle a dedicated endoscopic instrument or a unique sized device can be provided for every endoscopic procedure and significant variant thereof, in practice this is a significant increase in expense in an already expensive field, and is not a preferred solution to the problem of fit and security.

Moreover, a coaxial "collet" type of system, as described by U.S. Pat. No. 7,204,804 Zirps et al., is not very adaptable, and requires a number of exchangeable parts to be tried before a particular endoscope can be used with a particular adapter. This is not a desirable situation during surgery. The coaxial "collet" systems represented by U.S. Pat. No. 7,204,804 Zirps et al., while an improvement in instrument grip over a pure elastic ring or similar embodiment, for example as represented by U.S. Pat. Nos. 5,320,630 and 5,462,559 to Ahmed, still are limiting in that the range of locking variability of the "collet" device is limited by the amount of radial compression the locking collar can attain on the collet "fingers" over a fixed axial length of travel.

The prior art embodiments are also further limiting in their effect on the visual field of view once mounted. As described above, the visual lens is typically not centered on the centerline of the endoscopic instrument. Such off axis lens placement, combined with a cap on the instrument projecting more distal to the instrument distal tip, creates a limiting effect called "tunnel vision", due to looking through a tube where the walls constrict the field of view to a narrow central aperture. U.S. Pat. No. 7,189,247 Zirps et. al. has attempted to address this field of view problem by providing an extendable and retractable feature holding devices to be deployed. It is still utilizing the basic endoscopic instrument coaxial "collet" or elastic boot mounting principles previously discussed.

U.S. Pat. No. 7,189,247 Zirps et. al. clearly describes a portion of the delivery system which has operator controlled axial movement. The practice of operating the extending mechanism to create space that allows tissue to be drawn into a chamber for fastener attachment can lead to some confusion by the operator as instrument position of the distal tip (device length) along with field of view and focal distance of the optical system is changing device during actuation. This mechanism requires operator interaction and activation for proper function and result. When space within the body cavity is limited such extension movement needed may not execute fully or may cause trauma or inadvertent loss of distal tip location. As such, the requirement for movement of the instrument distal tip thus changing the working length when in the body cavity to generate a "tissue cavity" as a required by U.S. Pat. No. 7,189,247 Zirps et. al. is therefore a distinct disadvantage.

There is a need for visualization to be improved with endoscopes carrying adapters. There is a need for a reduction in the complexity and time of mounting tissue closure devices to endoscopic instruments. There is a need for any endoscopic mounted device to be positioned and locked quickly, easily and securely to the distal tip of the endoscope regardless of instrument size, and there is a further need for such an endoscopic mounted device to hold firmly and ensure a fixed instrument axial working length.

Endoscopes are purposefully designed with an extremely wide angle lens to provide the clinician with as much view of the tissue and surrounding environs as possible. In the delivery of bands, clips and the like, in order to provide that wide view, the endoscopic instrument should in principle be located distally and matched to the device distal tip. In practice this is not usually feasible, because with many closure devices described in the art, tissue needs to be drawn into a center zone of the deployment housing, to where the endoscope is located, to provide an effective closure. As a generalized well known procedure technique with a successful history of application and therapeutic result, it is a preferred clinical method. Therefore, the endoscopic instrument must be positioned some distance proximal to the overall distal tip of the delivery device when actively engaging tissue for the purpose of effecting tissue manipulation or closure and therefore in that configuration or use the endoscope has a limited field of view.

The preferred embodiment of the invention is designed to meet the expressed need for improved field of visualization, reliability ease of use and reduced complexity, adaptability to wide range of endoscopic instruments as compared with current art. The novel features and functionality of the invention include several improvements over the art.

One aspect of the invention is to provide improved mounting means, to allow more flexible pairing of particular endoscopes or endoscopic instruments with devices to be carried on their exteriors, while maintaining a tightly locked position of the external device on the instrument.

In another aspect, the invention provides the ability to mount such devices onto instruments where the distal portions of the instrument may have a highly variable geometry within the mounting area. Such geometry may include highly conical features, convolutions, or tapered configurations on the endoscope, therefore requiring such an adapting capability to sufficiently engage the instrument.

In another aspect, the invention provides the ability of the mounting device itself to easily adapt to a wide range of endoscopic instruments using a single universal mounting system, thus providing the clinician with the capability of changing an endoscopic instrument size within a procedure without needing to have multiple matching adapters to mount on such instruments.

In another aspect, the invention provides a clinician with an improved wide angle viewing capability in order to attain true peripheral visualization capability even after the mounting of an adapter onto the endoscopic instrument.

In another aspect, the adapter is diametrically flexible and compliant yet axially rigid, and thereby can engage a wide range of instruments and instrument shapes. The invention further provides mechanisms, geometric relations, and securing systems to allow a lateral offset of the axis of the adapter from the axis of the endoscope. This may be accomplished by the use of features, singly or in combination, selected without limitation from device stops, non-symmetrical geometries, non-closed cross-section geometrical constructs, isotropic and non isotropic materials configured into non-isotropic geometrical shapes, and combinations of closed and non closed perimeter feature geometry.

The geometric properties and flexible fitting capability of the adapter enables a wide range of endoscopic instruments to be located and secured by a single embodiment design, which may assume numerous possible configurations and orientations. In particular, the endoscopic visual lens, known in the art to be located off the centerline axis of the endoscope instrument, may be purposefully rotated and aligned with features of the invention intended to enhance and expand the visual field of view compared to prior art. This adaptive feature enables a wide range of devices, instrument guides, medicaments, delivery apparatus and the like to be integrated into the attachments of the invention, and thereby to be mounted, controlled, positioned and delivered using a single size embodiment device, thereby creating an endoscopic instrument with multifunctional capability and a wide angle field of view. A system for accomplishing this is described and claimed herein.

SUMMARY OF THE INVENTION

An adapter for attaching devices to the distal end of an endoscopic instrument is described. The adapter comprises a distal stop to limit the penetration of an endoscopic instrument into the adapter, and thereby fixes the location of the distal end of the endoscopic instrument relative to the adapter. In one embodiment, the distal stop can be a short cylinder or ring of a medical grade plastic, with a central hole or other lumen which is small enough to block the passage of the smallest instrument (endoscopic or otherwise) which is rated for use with the stop. In another embodiment, the stop is generally cylindrical in shape, but not closed. In another embodiment, the stop has openings in its side. In another embodiment the stop may include any or all features of the previously described embodiments plus at least one projection or rib like feature occupying a portion of the circumference or perimeter of the previous described embodiment which engages the endoscopic instrument. A preferred adapter consists essentially of a single device having at least a distal stop and attaching means for attaching said device to an endoscopic instrument.

The adapter further comprises at least one flange projecting proximally from said distal stop. The flange or flanges in their relaxed state have a diameter close to that of the distal stop, and may be formed integrally therewith. However, the flanges can flare outward as an endoscope is pressed into the adapter, so that the instrument enters the adapter flanges to a predictable extent, which is dependent on the instrument's average distal diameter, but not on the detailed diameter or any roughness. In most uses, the distal tip of the endoscope may be separated from the distal stop feature's most axially distal surface by a significant distance, due to the action of the flanges, or may be separated by specific geometry located on, attached to, and/or projecting from the distal stop embodiment feature which may project axially in the direction of the flanges, such a feature purposefully intended to limit the depth of axial penetration of the endoscope into said flange portion.

Such limiting geometry may be an embodiment typically occupying a portion of the circumference or perimeter of the flange and/or stop embodiment and may be integral or separate from either, or may be a separate component inserted by the user from the proximal or distal end for defining a set distance of the endoscope within the device. An endoscope depth limiting functional distance provided by this feature or the stop embodiment and flange alone where no additional feature is present may for example be about five to about twenty millimeters.

The centerline of the endoscopic instrument is purposefully misaligned with the virtual centerline of the invention, allowing a lens of the endoscope, or other optical detector, to be located closer to the outer diameter of the invention in order to facilitate an enhanced visual field of view when in a proper rotational alignment to other features. In a preferred embodiment, the distal stop and endoscope depth limiting features may be tapered along the center axial length to gradually decrease its diameter, distal to proximal, to create an offset for field of view enhancement.

The flanges are attached to the distal stop by any convenient means compatible with a use inside the body. In a preferred embodiment, the flange may be co-fabricated with the distal stop, so that both functions are contained in the same object. Such a device can be made by injection molding or similar means, or by partially sealing one or more sheets of plastic together to form a stop at one end and having one or more flanges at the other. In other embodiments, flanges can be connected to distal stops by any convenient joining mechanism. Examples of joining mechanisms include, without limitation, one or more of heat or pressure induced fusion, partial melting, spot welding, adhesives, solvent softening, stapling, stitching, punching, and use of fasteners.

The adapter can preferably accommodate endoscopes varying in diameter over a range wherein the largest diameter of endoscope that can be accommodated by the adapter is at least 150% of the smallest diameter of endoscope onto which the adapter can be reliably stabilized.

A preferred flange is a thin sheet of plastic. In alternative embodiments, functional equivalents of the flanges include inflatable bags, wires, wire cages, shape memory alloy, static meshes, or generally any material configuration construct or embodiment which exhibits a sufficiently rigid axial stiffness combined with sufficiently flexible or complaint diametrical properties transverse to the axis.

In addition, the adapter of the invention may preferably carry securing means for maintaining a desired degree of contact between the flange or flanges and the shaft of the endoscope, after the endoscope is inserted into the adapter. A preferred securing means is a rubber band like embodiment, but many alternatives are possible. The securing means does not engage the flange feature in a manner well known in the prior art, i.e., by annular uniform radial o-ring like compression, as described for example in U.S. Pat. No. 7,204,804 Zirps et al. Instead, the securing means preferably occupies only a portion of the device circumference and engages with the flange at defined attachment locations. Therefore, it is not required that the securing means be pre-loaded onto the endoscope, in contrast to the teaching of U.S. Pat. No. 7,204,804 Zirps et al. Hence, the securing means can be easily applied and removed even with the adapter positioned on the instrument, a distinct improvement over the art. Moreover, in the preferred embodiment of the invention, it is not a requirement for the flange to occupy a significant circumferential region of the adapter, or to provide an annular mounting feature which is required to properly engage prior art securing means.

The flange or flanges are deployed in a configuration which exhibits non-isotropic properties as a function of direction such that the axial direction is resistant to buckling or deformation from axial compression forces while being sufficiently compliant and highly flexible capability to absorb deformation radially without failure by transverse generally diametrical expansion or contraction movement. When such a material is connected to a stabilizing "stop" feature at the distal end, and an endoscope is placed into the embodiment creating some natural deformation, the fit of the material on the endoscope and the grip of the material on the endoscope is now sufficient to secure the endoscope instrument distal end from inadvertent release.

A further application of generally radial forces to the flange feature at the proximal end of the embodiment elongates the axial length of contact between the endoscope and the flange feature, thus providing a large surface area of contact, and a secure attachment.

Such an idealized flange geometry providing these features is best represented and described as a circumferential portion of a hollow cylinder wherein the curvature of the generally arcing portion of the cylindrical embodiment (the directrix) in the definition of a cylinder easily resists buckling from axial forces induced along its axial length (the generatrix). (See definition above). However, in the transverse direction, the embodiment is flexible and more readily diametrically displaced. A typical geometry for a flange feature providing these critical properties therefore may be curved in the direction perpendicular to the endoscope axis, and will typically comprise at least one attachment point for a securing means to impart additional reactive radial force. The attachment point or points for this embodiment will typically be located towards the proximal end of the flange. In a preferred embodiment, the securing means does not engage the endoscope in an annular fashion slidably engaging and disengaging, as in prior art, nor is it a secondary closed cylindrical element slidably deployed over tapered flange finger constructs to generate radial forces. The securing means in the preferred embodiment provides a radial force to the flange embodiment by being a tension generating non-closed cross section construct, which is attached to said flange embodiment at one or more distinct attachment points such that the securing means may be attached and removed without the need for any axial motion of the endoscopic instrument alone or in concert with the device when mounted on said endoscope.

"Securing means", as used herein, are any device features which increase the interaction of the flanges with the surface of an endoscopic instrument, so that when the flanges are secured, it becomes very difficult to remove the flange from the endoscope, or to rotate or slide the flange with respect to the endoscope, without first releasing the securing means.

In a preferred embodiment, the securing means may be any form of Elastomeric, or otherwise constricting spring like or force generating means which, when in communication with identified endoscopic interacting features of the present invention, enable and assist those features in attaching and locking to the endoscopic instrument. The securing means itself may also provide some additional attachment and/or stiction property to the preferred embodiment of the present invention's attachment function.

In a preferred embodiment, the securing means consist of a closed elastic band, or ring like construct and the attachment points are hooks, preferably located towards the proximal end of the flanges. After the endoscope or other instrument is pressed into the flanges, the elastic band is caught on a first hook, then wrapped around the instrument, and then caught on the same hook or on a second hook. This procedure forces the flange or flanges to close against the outside of the instrument, at a location significantly proximal to the instrument's distal end. The function of the securing means in the invention is to forces the flange or flanges to close against and follow (hug) the outside surfaces of the instrument, thus engaging the flanges and the instrument and securing the adapter from movement. This may be accomplished a number of different ways using elastic or spring like embodiments made of many different materials and designs which, engaging with the flange geometry, provide this result.

The securing means are preferably somewhat elastic, and could be as simple as a rubber band or O-ring. The securing means could also mount onto the flange by other means, or could be integral to the flange or could be hinged to the flange, and do not have to be elastic, but could be adjusted by other means to provide the securing function. The flange or flanges, if made of an appropriate material, or having a suitable surface treatment or surface texture, will be resistant to movement upon the surface of the instrument, thereby providing increased stiction properties (i.e., an increased force is required to cause one body in contact with another to begin to move), especially after being pressed against the instrument by the securing means. However, it is also preferable that the flange material not strongly bind to the endoscopic instrument without application of such a force, to enable easy assembly.

In an embodiment that is especially preferred for endoscopic uses, the flange is made so that when it is secured to the shaft of the endoscope or other instrument, a viewing area is left open. This may be a location on the instrument not covered by the flange, or an area of the flange constructed to have good optical properties. Then, during the securing of the adapter to the instrument, the adapter is easily rotationally oriented on the instrument so that the viewing area is located in proximity to a preferred area of the instrument, for example a light receptor, such as a lens.

Then, when the instrument is inserted and conveyed to the appropriate tissue location, the lens or other light receptor is able to convey images of local tissue, such as the inside of a natural orifice or lumen, to the operator. While viewing through the distal stop of the adapter is possible, the lateral view is restricted, and the enlarged lateral view provided by the viewing area is a significant help to the operator in selecting the correct location of the instrument for performing the procedure. In an alternative preferred arrangement, the embodiment may be totally covered by a flexible elastomeric sheath during or after the endoscopic guiding instrument is mounted. This sheath provides a number of advantages, in particular that suction can then be used to control tissue regardless of endoscope size used. Also, the sliding members are now covered, presenting an atraumatic surface to the local anatomy. If the sheath is optically clear, then the endoscope is still able to visualize in a lateral manner if desired. Such a sheath-like embodiment preferably is flexible enough so as to not impair the motion of the deploying members, yet provides a smooth surface for passage of the instrument into and about the body.

Generally, the invention comprises an adapter for attaching devices to the distal end of an endoscopic instrument, the adapter comprising distal stop means to limit the penetration of said endoscopic instrument into said adapter; wherein the adapter is constructed so that the central axis of said adapter and the center axis of said endoscopic instrument are not concentric when said adapter is mounted on said instrument. The adapter consists essentially of a single device having at least a distal stop and attaching means for attaching said device to an endoscopic instrument. The adapter is constructed so that the central axis of said adapter and the center axis of said endoscopic instrument are substantially parallel but not coaxial when said adapter is mounted on said instrument. The distal stop means may have a closed perimeter, and at least one flange projecting from said distal stop means, wherein said flange comprises securing means to secure said flange to said endoscopic instrument to prevent motion of said flange with respect to said instrument. The flange may be comprised of a material flexible enough to at least partially encircle an endoscopic instrument circumference, said encirclement being sufficient to allow the securing of the adapter to the distal end of endoscopic instruments having a range of diameters and shapes at their distal tips. The flange may have a non-closed perimeter. The perimeter may have at least one opening, and the distal stop may also a perimeter with at least one opening, and the openings of the flange perimeter and the distal stop perimeters may be aligned.

The adapter typically has securing means, constructed and arranged to provide a force that is sufficient to impede movement of said adapter with respect to said endoscope, when said adapter is placed on said endoscope and said securing means is engaged with said adapter. These securing means may be one or more of an o-ring, a wrap around, an overlapping wrap around, a hook-loop closure, at least one hook or snap closure, an elastomeric material, a thermoplastic material, a thermoset material, a super-elastic material, a metallic material, an adhesive material, an inflatable element, a collapsible shrink wrap, a welded in place securing means, a cut or sever to remove securing means, or any combination thereof.

The adapter has one or more flanges, which preferably after being secured to the endoscopic instrument, comprise at least one region which is open or sufficiently transparent to allow visualization of tissues surrounding said endoscopic instrument by visualization means mounted on said endoscopic instrument. The adapter may further comprise a sheath covering said adapter. The adapter may be used to attach one or more devices to an endoscopic instrument to allow specific functions to be performed at a tissue site located remotely in the body. The device attached may comprise one or more of a tissue fastener, or a dispenser therefor; additional lumens for access to the operative site; functional means to dynamically resize or reconfigure the attached device portion; drug delivery or medicament dispensing means; energy delivery means; sensor or measurement devices; visualization means; and markers to assist in determination of the location of the endoscope tip. Connecting means between the device and the adapter may include without limitation one or more of co-fabrication, mechanical assembly of discrete function components and sub assemblies, bonded assembly of discrete function components and sub assemblies, fused assembly of discrete function components and sub assemblies.

The adapter may be used with an endoscope which is selected to be larger in diameter than the distal stop effective diameter and wherein a flange, when in contact with said endoscopic instrument prevents proximal to distal movement of the endoscope with respect to the flange. Alternatively, the endoscope is selected to be no larger in diameter than the distal stop, and the flange, once in contact with said endoscopic instrument and secured on said instrument by the securing means, prevents both proximal and distal movement of the endoscope with respect to the flange.

In another embodiment, an adapter for attaching devices to the distal end of an endoscopic instrument comprises at least a distal stop means to limit the penetration of said endoscopic instrument into said adapter; at least one flange projecting axially from said distal stop means; and a securing means for locking said adapter on to said endoscope. Preferably, said flange comprises a non closed cross-section portion of a generally hollow cylinder.

In another embodiment, an adapter for attaching devices to the distal end of an endoscopic instrument comprises a distal stop means to limit the penetration of said endoscopic instrument into said adapter; at least one flange projecting axially from said distal stop means; a securing means for locking said adapter on to said endoscope; and an attachment means for engaging the securing means, said attachment means located proximal to said distal stop means.

An adapter may have a flange which covers more than 180 degrees of the circumference of an endoscopic instrument, and at least a portion of the flange may be optically transparent. The adapter can accommodate endoscopes varying in diameter up to about 50%. The flange is arranged to have a highly expandable portion to accommodate the insertion of an endoscopic device having a diameter greater than that of a distal stop. After the binding of a flange to an endoscope, a sealing property is created between said adapter and said endoscope sufficient to allow suction to occur at the distal end of said endoscope upon provision of a vacuum to said endoscope at its proximal end. The flange may be arranged to have a highly expandable portion which is visually clear. The flange may be arranged to have a highly expandable portion which overlaps an expandable flange portion, and typically will have at least one slit.

In another aspect of the invention, a method of conveying a device to a remote location in the body using an endoscopic device is provided. The method may comprise providing an adapter for attaching a device to be transported to an endoscope, said adapter consisting essentially of a terminal stop, a flange, means for attaching a device to said adapter, and means for attaching said adapter to an endoscope; attaching a device to be transported to said adapter; attaching said adapter to said endoscopic instrument; and delivering said device to said remote location using said endoscope.

The means for attaching the flange to the endoscope may be selected from mechanical assembly of discrete function components and sub assemblies, bonded assembly of discrete function components and sub assemblies, fused assembly of discrete function components and sub assemblies or any combinations thereof.

The adapter may provide means for lateral visualization of tissue through the side of said flange, through one or more of an opening or window, and an optically transparent material. The adapter may be constructed so that the central axis of said adapter and the center axis of said endoscopic instrument are not aligned when said adapter is mounted on said instrument.

In another aspect, the invention provides a method of manufacturing an adapter. The adapter consisting essentially of a terminal stop, a flange, means for attaching a device to said adapter, and means for attaching said adapter to an endoscopic instrument, and the method of manufacturing is selected from one or more of injection molding, insert molding, multi-material molding, casting, mechanical assembly of discrete function components and sub assemblies, bonded assembly of discrete function components and sub assemblies, fused assembly of discrete function components and sub assemblies or any combinations thereof. In the method, the adapter is constructed so that the central axis of said adapter will be essentially parallel to the center axis of said endoscopic instrument when said adapter is mounted on said instrument. The preferred manufacturing method ensures that the parallel axes of the adapter and the instrument will not be concentric, and the adapter may consist essentially of a single device having at least a distal stop and attaching means for attaching said device to an endoscopic instrument.

The adapter may further comprise a sheath or membrane covering the adapter proximally of the distal end of the adapter, which sheath may be deployed before or during a medical procedure. The sheath is preferably optically clear at least in part. The adapter may further comprise at least one delivery channel attached to said adaptor, said channel suitable for the conveyance of at least one of a fluid or an instrument from outside of the body to an interior site. The channel may be changed in functional cross section by one or more of mechanical manipulation and inflation by gas or liquid.

An adapter for attaching devices for dispensing tissue fasteners to the distal end of an endoscopic instrument can comprise:

a distal stop means to limit the penetration of said endoscopic instrument into said adapter;
at least one flange projecting axially from said distal stop means;
a securing means for locking said adapter on to said endoscope; and
said adapter can carry a deployment assembly activated by actuating means operated from outside the patient by a wire sheath connected to a pusher, wherein said pushing said pusher into said deployment assembly pushes a tissue-affixing clip out of said assembly.

BRIEF DESCRIPTION OF THE FIGURES

FIG. 8 shows a side view of an alternate configuration for an endoscopic attachment.

FIG. 9 is an isometric view of FIG. 8,

FIG. 10 is a cross-section view of FIG. 8, and

FIG. 11 is an expanded view of the flexible endoscopic clamping feature of FIG. 8, useful in providing a seal.

DETAILED DESCRIPTION OF THE INVENTION

Figure 1:
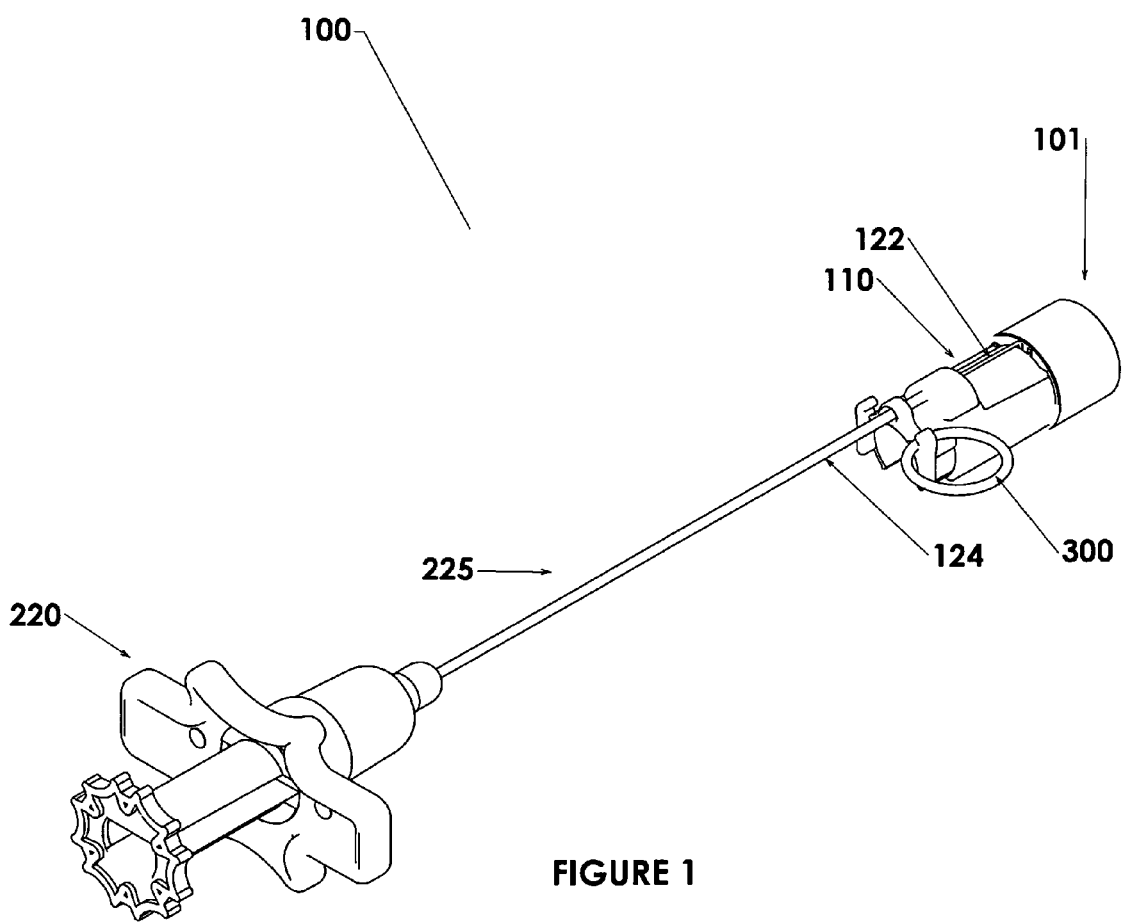
FIG. 1 is an overall view of an example of an adapter of the invention which is configured to deliver a device.

Particular embodiments of the invention are described in detail to enable the reader to understand the invention. In FIG. 1, an endoscopic instrument 100 is shown. This particular endoscopic instrument, generally described in priority document U.S. 61/199,606, is designed to deliver a tissue clip to close an opening created during surgery, but the apparatus and method for affixing the clip delivery assembly to an endoscopic instrument are more general.

In FIG. 1, the device 100 has a handle assembly 220, with actuating means 225 connecting it to a deployment assembly 101. In this embodiment, the actuating means 225 comprise a wire sheath 124 and a wire 122. The wire sheath 124 is connected to pusher 110, which in this embodiment pushes a tissue-affixing clip out of assembly 101. The securing means 300 is in this instance an elastic band, shown in a non-securing position. The length of the actuating means 225 will be selected to be compatible with the length of the particular endoscope and procedure to be performed, thereby typically requiring the device 100 to be available with more than one length of actuating means 225.

Figure 2:
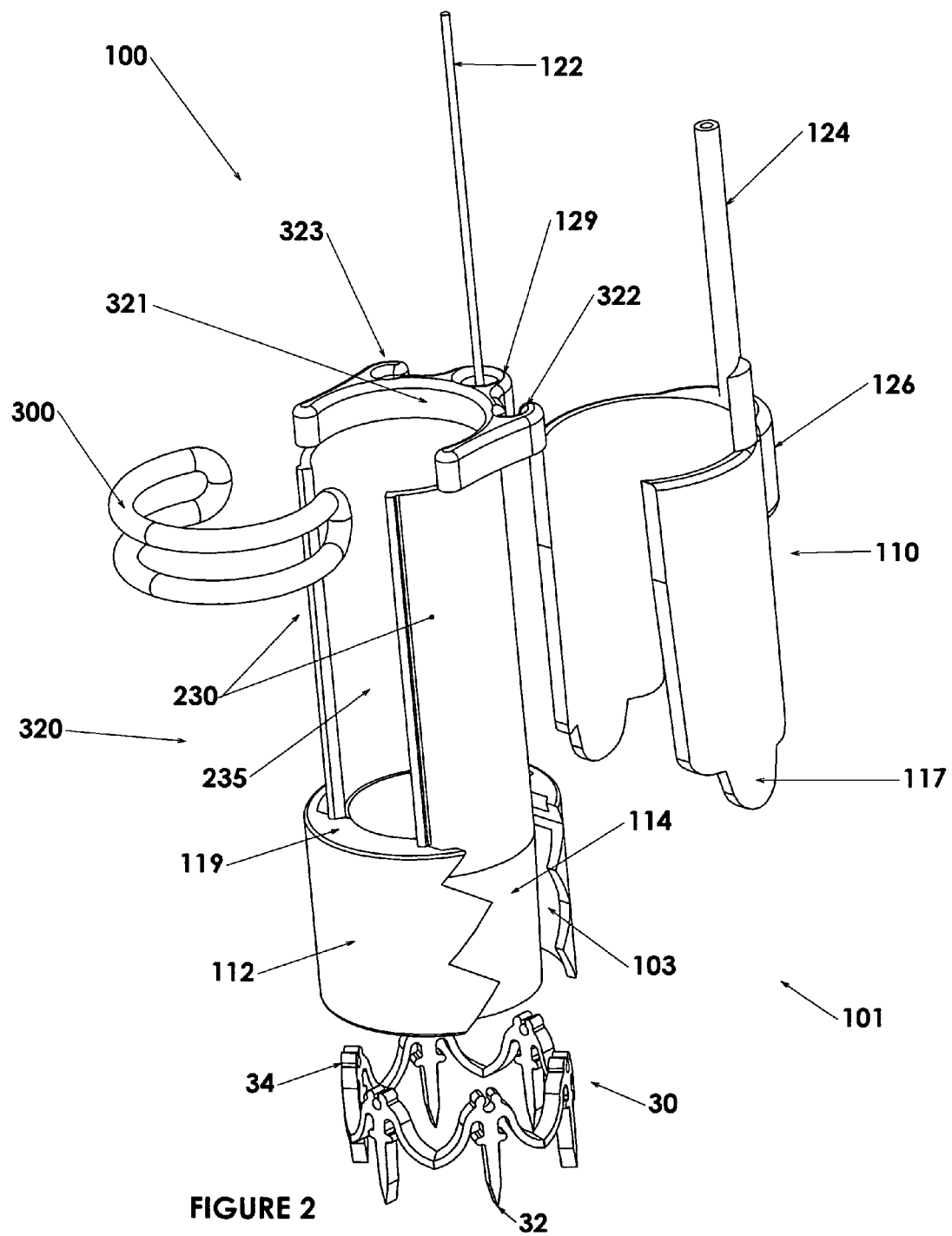
FIG. 2 shows an exploded view of the distal end of FIG. 1.

FIG. 2 shows an exploded view of the distal end of the device 100 of FIG. 1. In this particular embodiment, the deployment assembly 101 includes a tissue fastener device 30 with barbs 32 and projections 34, as described in commonly assigned US patent publication 2007/0225762. The fastener fits in an annular space 103 defined by outer shell 112, inner shell 114, and connecting wall 119. The fastener is deployed by a deployment sleeve or pusher 110, which is connected to wire sheath 124 via connector 126. The contact areas 117 may be pushed into the annular space 103 to deploy the tissue fastener. These parts are specific to the particular application illustrated, and typically would not be present in other endoscopic devices.

In FIG. 2, the attachment adapter, generally designated as 320, is shown in detail. In FIG. 2, an adapter 320 comprising a single flange 230 is shown. Flange 230 is a "C-shaped" part-circle in profile, having more than a half-circle of circumference, and has a longitudinal opening 235. Opening 235 provides a viewing area, as well as providing flexibility so that the flange 230 can be conformed to an endoscope. The fastener assembly in this embodiment also includes a proximal connecter 321, which carries a sleeve guiding means 129 for the wire sleeve 122, and two connecting hook-like members 322, 323 for an elastomeric connector 300. At its distal end, the flange 230 is joined to the connecting ring 119. Ring 119 is where inner shell 112 and outer shell 114 proximally terminate, thereby defining an annular space 103 between them. In this embodiment, the connecting ring 119, defining the proximal boundary of annular space 103, may also provide the distal stop function. In addition; residing within the connecting ring 119 is an attachment point (not shown) for wire 122.

Figure 3:
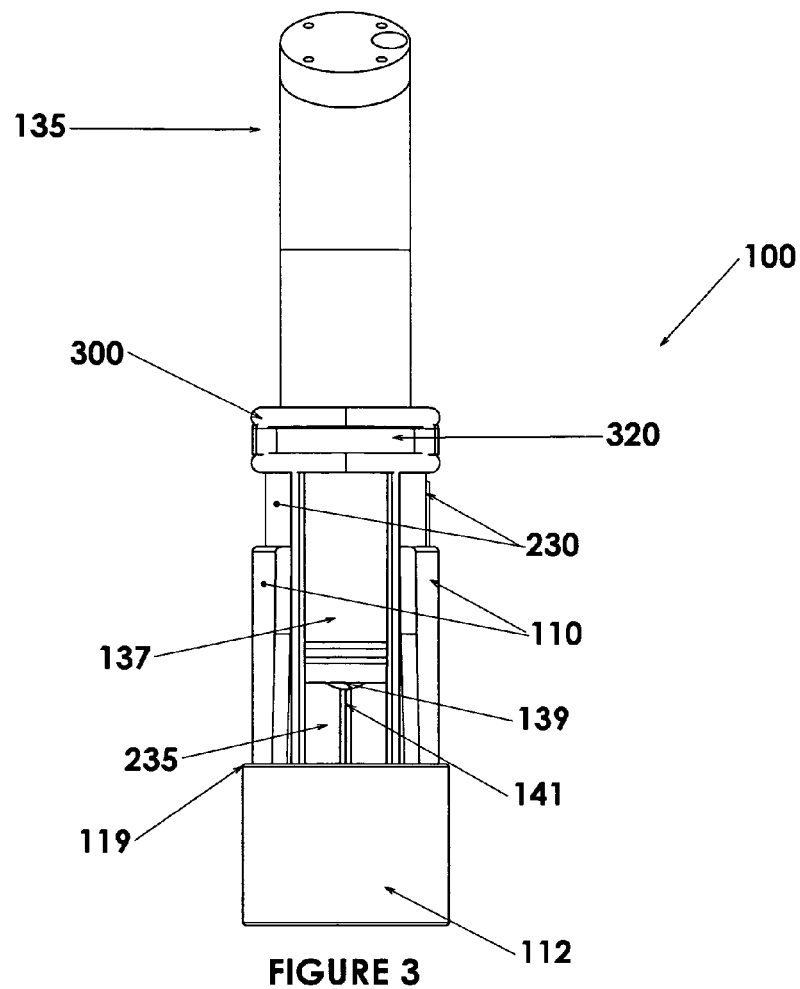
FIGS. 3 and 4 show the adapter of FIGS. 1 and 2 with an endoscope inserted into the adapter, particularly showing optical elements with a lateral viewing area.
Figure 4:
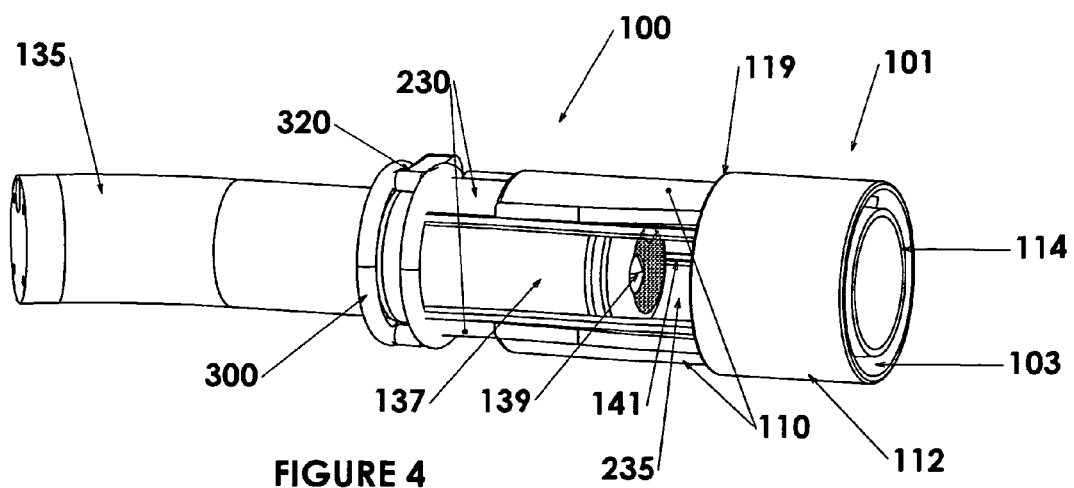

In FIGS. 3 and 4, respectively side and isometric views of the clip delivery system of FIGS. 1 and 2, an endoscopic device 135 is shown, with features typical of an Olympus XGIF-Q160Y9 single channel endoscope at its distal end 137, as well as the attached adaptor 100. The elastomeric connector 300 has been closed around the shaft of endoscope 135 and is holding flange 230 in contact with endoscope 135. Part of the endoscope 135, i.e. distal end 137, can be seen through opening 235 in the flange 230, including a lens 139.

A raised area 141, located on the inner surface of the flange 230, provides part of the distal stop function by limiting the distal movement of distal end 137 of endoscopic device 135. Additionally, depending on the size of the endoscopic instrument, the endoscope position distal stop function may otherwise be provided by the connecting ring 119 feature in this embodiment, or may be a separate element with the stop feature placed some distance along feature 141 at a distance proximal to connecting ring 119.

With the elastomeric connector 300 in place, the flange 230 of the adjustable fitting is pressed tightly against the endoscope 135, thereby preventing any motion of the fastener deployment assembly 101 with respect to the endoscopic device 135, aside from ejection of the fastener 30.

As can best be seen in FIG. 4, the provision of the opening 235, in combination with a distal stop functionality, allows visualization of the tissue surrounding the endoscope, through the opening 235 of the embodiment as well as the conventional view of the particular target tissue available by looking axially through the center clear volume of sleeve 230 and the inner annular shell 114.

The endoscopic instrument shown in FIGS. 3 and 4 is generally close but not an exact match in diameter to the 'at rest' geometry of the preferred embodiment and represents an idealized size instrument for its class and functionality. As such the inherent variability in the diametrical sizes of the instruments in a given class will effect the amount of axial offset between the instrument centerline and the embodiment centerline as the axis are purposely by design in the preferred embodiment not intended to be coaxial, however, the optical imaging lens already being offset within the instrument itself can still be aligned with feature 235 to enhance the peripheral viewing capability. This unique capability of the invention is more dramatically illustrated and understood in FIGS. 5, 6 and 7.

The opening 235 may contain no material, or may be arranged to have an optically clear material covering it to prevent passage of fluids through the opening. The additional off axis peripheral viewing capability takes advantage of the wide angle view characteristics of state of the art endoscopic instruments. This expanded view is extremely helpful to the endoscopist in finding the target area and achieving the proper distance from the operative site.

The distal position of the endoscopic instrument relative to the adapter's most distal end may vary as a function of instrument size and by design may be intentionally controlled within a singular attachment adaptor embodiment by the definition and location of features 141 and 119. Such capability is highly desirable and provides a "universal attachment adaptor", fitting numerous instruments with optimal functional location of operating features. This function may also be obtained, for endoscopic instruments significantly larger in diameter than the distal stop, by the flexibility of the flange 230. Depending on the elasticity and thickness of the material of the flange, the penetration distance of the endoscope into the flange towards the distal stop is limited. There will be little variation in the final position of the lens 139 with respect to the wall 119 or other limiting feature of the distal stop, and so both functional optical viewing and well-controlled deployment of a device, such as tissue fastener 30, are possible without requiring complete reproducibility of instrument location within the attachment 320.

Any securing embodiment that enables and/or assists the flange means in gripping and attaching to the endoscope may be utilized in the design of the adapter. The securing embodiment alone in some constructs may be insufficient by itself to provide the required gripping and stiction forces to prevent an inadvertent disassembly or disengagement. However, when such a securing embodiment is used in conjunction with the highly compliant and adaptable flange embodiment geometry as described above, as a preferred embodiment of the present invention, then the combination of these features, their placement and performance provide a unique, superior and much more reliable endoscopic attachment means. It is preferred that the material or surface of the flange or flanges, and the force applied to the flange by the securing means, must be coordinated to provide sufficient resistance to movement (as "stiction" or other measure) to prevent excessive movement of the attachment with respect to the endoscopic instrument. Such attachment means are thereby made more widely applicable to the numerous sizes of endoscopic surgical instruments known in the art. Moreover, in some embodiments the flange 230 may have sufficient adherence to the surface of endoscope 135 to prevent easy removal of the adapter 320, without requiring a separate force applicator such as securing loop 300 or an equivalent.

Figure 5:
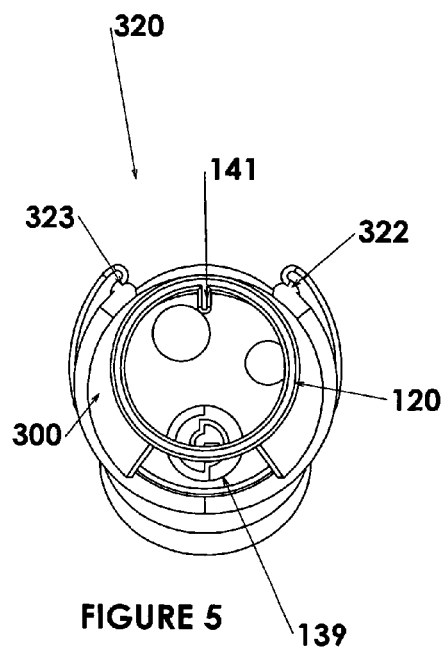
FIG. 5 is an isometric view of an adapter, showing details of the endoscopic instrument attachment, locating and securing embodiments of the invention in an isometric view.
Figure 6:
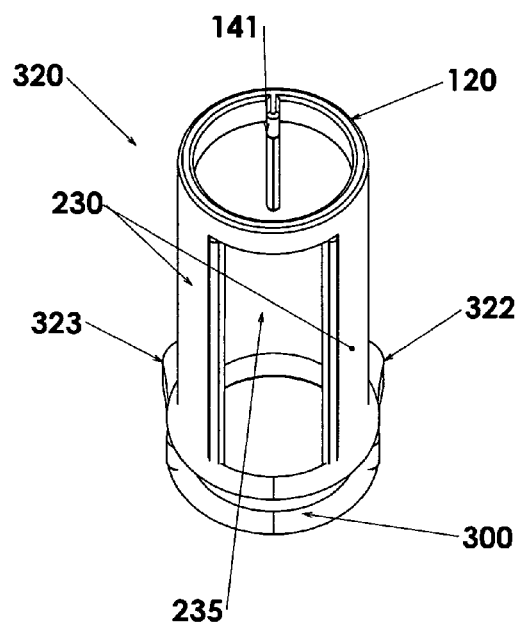
FIG. 6 shows an end view of the adapter of FIG. 5, with an endoscope inserted.
Figure 7:
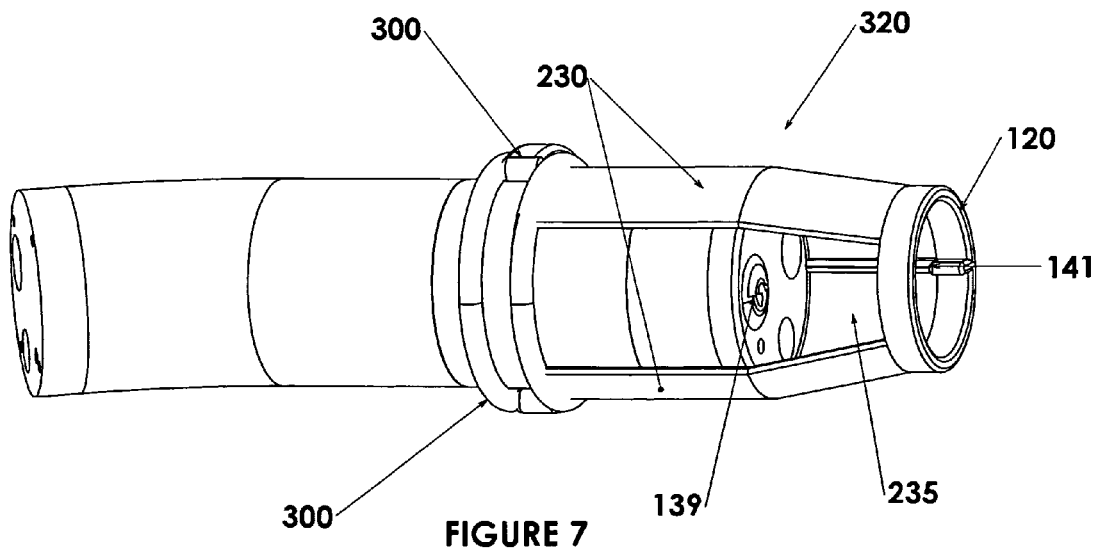
FIG. 7 shows a side view of an adapter on an endoscope, as shown in FIG. 6.

FIGS. 5, 6 and 7 illustrate the features of the adapter and their locations, and the enhanced effect of peripheral vision, and the adaptability of the attachment geometry when attaching an endoscopic instrument up to ⅓ larger than the preferred embodiment "at rest" dimensions. FIG. 5 shows an attachment adapter 320 for attaching devices to the distal end of an endoscopic instrument. The adapter comprises distal stop features 120 (ring) and 141 (raised internal protrusion or wedge) to limit the penetration of an endoscopic instrument into the adapter.

In an alternative construction, assembly and user preparation method, said scope penetration limit 141 may be a separate non-integral component, loaded in at the time of use to space the scope distally of distal stop 120. Such a component is inserted by the user to reside in front of the distal end of the endoscopic instrument, to specifically rest against distal stop feature 120, and be captured within the confines of adapter 320. Such an embodiment is intended, like the integral form of feature 141 previously described, to limit the depth of endoscope penetration by providing a robust hard stop property to feature 141; and in this embodiment, may be inserted by the user before the endoscopic instrument is loaded.

As shown in FIG. 6, the adapter 320 also has at least one flange 230 projecting proximally from said distal stop 120, said flange comprising at least one attachment point such as 322 and/or 323, optionally carried on carrier 321, for attachment of securing means 300.

FIGS. 6 and 7 further illustrate the adaptability of the invention when used with a 15 mm endoscope such as an Olympus GIF-2T160 or an Olympus GIF-Y0026, both gastric style endoscope instruments. These are significantly larger than the "rest diameter" of the flange, in this particular embodiment. The Olympus GIF2T160 representing this class of dual channel flexible endoscopic instruments is about 50% larger in diameter that the previous class of instrument illustrated in FIGS. 3 and 4 previously.

When mounted on the same adapter, the amount of axial offset between the instrument centerline and the embodiment centerline can be clearly seen. Furthermore, the visual lens already displaced axially within the instrument design is further displaced peripherally in the embodiment virtually into an open slit which has now assumed a more tapered like feature. These figures describe and illustrate the flexible flaring adaptable properties of flange feature 230, and the enhanced peripheral vision capability.

FIG. 6 shows the details of the endoscopic instrument attachment adaptor 320, for attaching devices to the distal end of a large dual channel endoscopic instrument 135 in a distal to proximal view, including locating and securing embodiments 300, 322, 323 of the invention. FIG. 7 is an isometric side view of FIG. 6 showing the peripheral visualization feature capability the axial offset of the endoscopic instrument and the invention, the functional adaptive features of the flange design and the use of the stop for axial position.

The adapter 320 again comprises distal stop features 120 (ring) and 141 (internal protrusion or wedge) to limit the penetration of the dual channel endoscopic instrument 135 into the adapter 320. The adapter 320 also has at least one flange 230 projecting proximally from said distal stop 120, said flange comprising at least one attachment point 322 and/or 323 for securing means 300. Dual instrument channels 138 in the endoscope 135 are shown; they are typically associated with instruments of this size, and it can be seen in this Figure that the instrument channels 138 are easily positioned in the adapter, such that instruments delivered from within them would pass through terminal ring 120 and thus a more or less along the centerline axis of the attached adapter.

In FIG. 6 and FIG. 7, also note the significant displacement of the endoscope center axis in relation to the ring 120 (to which a device to be delivered would be attached), and the extensive amount of peripheral vision available to endoscopic viewing lens 139 and the capability of the flange features 230 to adapt to the endoscopic geometry.

In other embodiments of the attachment adapter 320, the distal stop 120, which has a closed perimeter here, may have a non closed perimeter and also an internal limiter 141 limiting endoscope penetration. In other embodiments the securing means 300 are not elastomeric, or do not comprise loops. Securing means 300 may instead or in addition include springs, coils, wire or hinged integral and locking features attached to flange portion 230. Any embodiment which represents a non closed cross-sectional geometry, or a loop or closed perimeter geometry which can be configured to be attached and detached to the distal features 321,322 and 323 (in the preferred embodiment) or their functional equivalent, can provide the required radial forces to lock the endoscopic instrument with respect to the adapter.

Moreover, this can be done without requiring a rotational motion or movement of the adapter embodiment in relation to the endoscope to be used, either to apply or to remove the adapter from the instrument. Furthermore, this does not require an axial motion or movement to insert or withdraw said endoscopic instrument from said securing means.

Preferably, the at least one flange 230 defines a slit or window opening 235 allowing visualization of the surroundings through said opening by 139 endoscope vision lens, or equivalent, located on said endoscopic instrument 135.

FIGS. 8-11 illustrate an alternate configuration of the adapter 320, which can provide easy and secure attachment of an endoscopic instrument. Device delivery features have again been removed for clarity. Similarly to the capabilities and performance properties illustrated in FIGS. 6 and 7 with regard to endoscopic size adaptation, shown are the attachment adapter 320 for attaching devices to the distal end of an endoscopic instrument 135, the adapter comprising distal stop features 120 and 141 to limit the penetration of said endoscopic instrument 135 into the adapter, and at least one flange 230 projecting proximally from said distal stop 120, said flange comprising at least one attachment point 323 for securing means 300. In the attachment adapter 320, the distal stop 120 may have a closed perimeter, or alternatively the attachment adapter 320 may have a non closed perimeter embodiment together with the distal stop 141, as well as the previously described attachment adapter 320 where the securing means 300 are elastomeric.

As shown in detail in FIG. 10 and FIG. 11, the attachment flange in this embodiment features a combination of features and geometry with distinct properties which in total define a generally closed perimeter. The adapter comprises the open flange structural element 230 (hatched) attached to an expandable, thin, generally optically clear, non-structural but sealable connecting membrane 240, with sufficient folded-back or serpentine geometry 242 to enable easy expansion and contraction of the flange portion of the adapter diameter to accommodate varying endoscopic instruments being inserted within. Securing member 300, or any functionally equivalent means, when positioned onto the embodiment, can collapse said thin membrane features 240 and 242 and apply cincture forces to flange portion 230, thus securing and compressing the attaching devices of the attachment adapter 320 to the distal end of an endoscopic instrument [not shown].

The embodiment described in FIGS. 8 through 11 is especially suited to procedures requiring the application or use of vacuum in tissue manipulation, because the attachment adapter 320, once secured onto the endoscopic instrument 135, provides a sealed center conduit as a result of the added attached membrane 240. For optical visualization of the peripheral field of view for such instruments, an optically clear material would be used as membrane 240 or as part of flange 230 to maintain visual clarity.

Figure 12A:
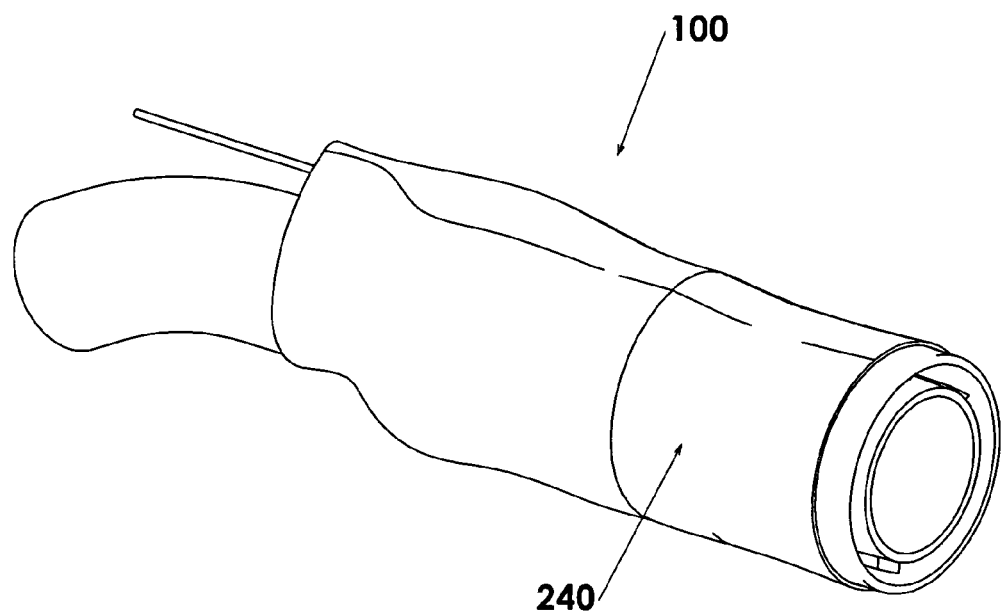
FIGS. 12A and 12B show an alternate construction method for the device of FIG. 8.
Figure 12B:
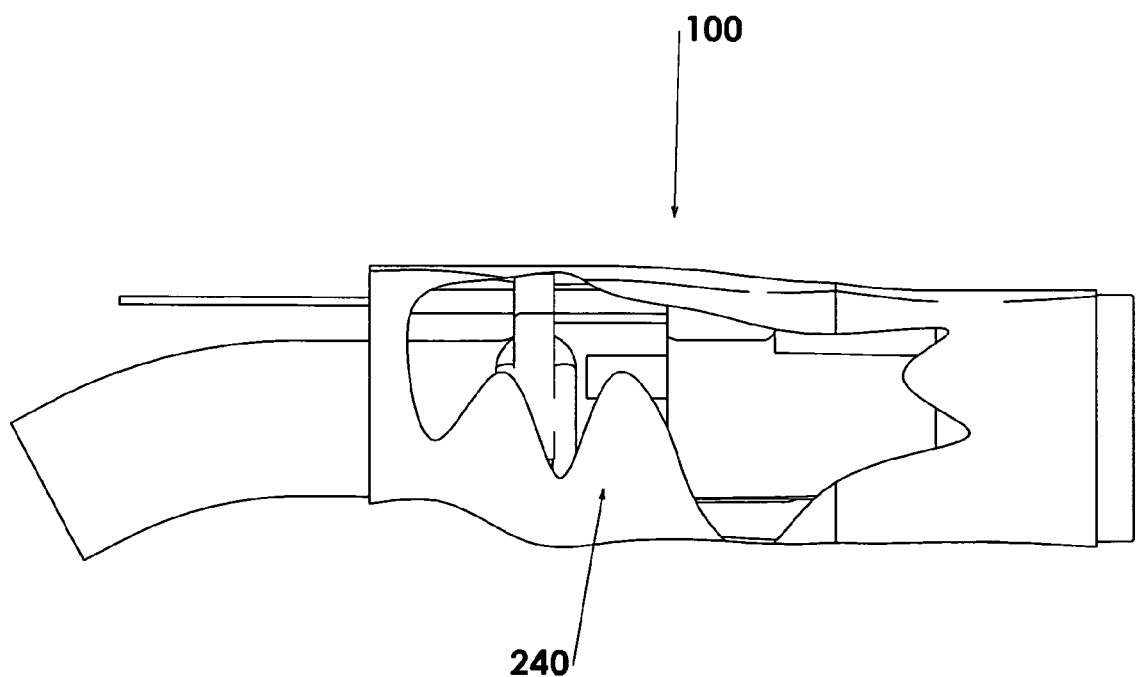

FIGS. 12A and 12B (a cutaway view of 12A) are an alternative construction and assembly method for devices used in procedures requiring the application of vacuum. In the preferred embodiment of FIGS. 12A and 12B, a membrane feature 240, in a variant of the membrane (240) shown in FIGS. 10 and 11, consists of a sheath 240 covering the distal portion of endoscopic instrument 100. The sheath is flexible, approximately cylindrical, optionally optically clear, and preferably at least somewhat elastic. The membrane sheath 240 may be integral to the deployment assembly, pre positioned as a sleeve or rolled up construct that can be unrolled distal to proximal, (or alternatively proximal to distal), or may be a separate construct that is placed on the distal portion of endoscopic instrument 100 using well known sheath or condom like loading and unrolling techniques before or after the endoscopic instrument 100 is located and secured on the endoscopic instrument.

Figure 13:
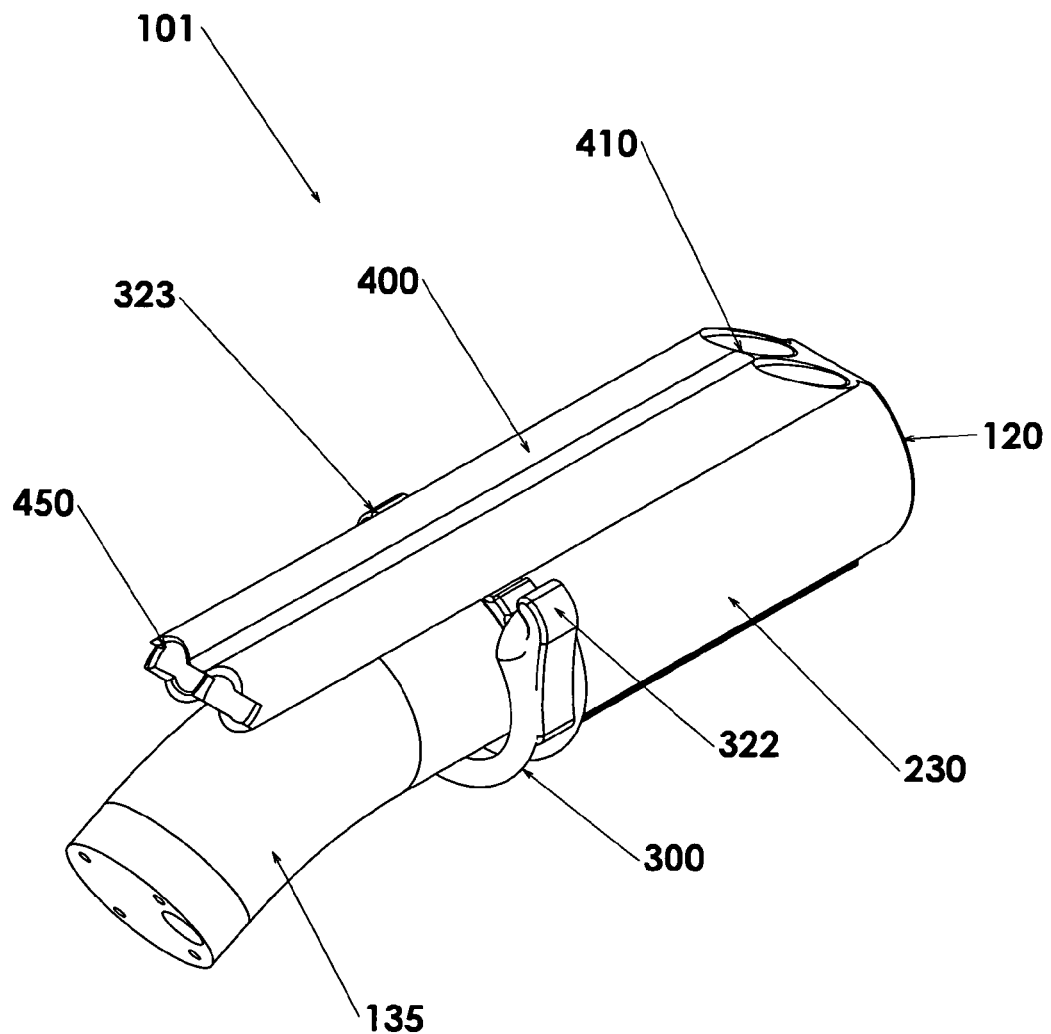
FIG. 13 shows an embodiment in which the adapter is used to carry extra channels to the operative site.

FIG. 13 illustrates an example of an alternate configuration of the device having additional functions. The device of FIG. 13 is similar to previously described embodiments, such as that of FIGS. 5-7, further comprising integrated dual delivery channels 400 attached to attachment adapter 320. These delivery channels 400 allow the passage of instruments or fluids from outside the body to the instrument channel distal tip 410. The instrument delivery channels 400 (shown truncated at position 450), are typically the same length as the endoscopic positioning device. This is a convenient means for adding extra channels to an existing endoscope, providing the physician with two additional delivery channels which are controllable by the endoscopic instrument.

Other such constructs which may replace feature 400 may be singular or multiple instrument channels of numerous sizes which can be expanded and contracted in diameter to change directions or provide a wider tissue manipulating platform by using mechanical manipulation and/or inflatable or hydraulic mounting schemes. This allows the tube profile to be in a minimum profile state for passage to a tissue site, after which the tube size is expanded to a maximum condition once through the natural constrictions of the body orifices. For example, and without limitation, the extra channels 400 could be made of a tough but flexible fabric or membrane, to allow passage of devices or fluids.

These examples are but some of the types of controls, instruments and medical device embodiments which may be controlled and manipulated with confidence due to the secure attachment function of the present invention. The securing function may be performed by any mechanism suitable for reversibly attaching an adapter to an endoscopic device, including but not limited to springs, clamps, clips, wire, wire-ties, ratchets, adhesives, Velcro hook-loop fasteners, or tapes. Securing means will typically be constructed from medical grade plastic, fabric or metal, optionally including coatings or other surface treatments to achieve surface properties suitable for obtaining the desired functional properties. For example, a prototype flange, found to be suitable, was made from an injection molded polypropylene thermoplastic material approximately 1 mm in thickness. This flange was secured using an elastomeric O-ring, approximately 1.5 mm in thickness and with a diameter about the same as, or slightly less than, the diameter of the endoscope.

The securing means 300 is portrayed herein as a rubber band, but is not so limited in the invention. The securing means can be any material or device that is constructed and arranged to provide a force that is sufficient to impede movement of said adapter with respect to said endoscope when said adapter is placed on said endoscope and said securing means is engaged with said adapter. The securing means 300 may for example be one or more of, but not limited to, an o-ring or elastic band, a wrap around material, optionally overlapping, including hook/loop material (e.g. Velcro™ fabric), or equivalent. A cuff, preferably somewhat elastic, can be slid over the adapter, including optionally the flange, to bind it to the endoscope with sufficient firmness. Attachment means can also be one or more snaps, hooks or other simple connectors. It may be an elastomeric material, a thermoplastic material, a thermosetting material, a super-elastic material, or a metallic material. It can be an adhesive material, an inflatable or hydraulic actuated inflatable device, a collapsible shrink wrap, a welded in place connector, a cloth or fiber or strand which is cut or severed to remove it, or any combination thereof. Adhesive, preferably reversible, can be used to enhance adherence of the flange to the endoscope.

In a preferred embodiment, an adapter for attaching devices for dispensing tissue fasteners to the distal end of an endoscopic instrument can comprise at least:
a distal stop means to limit the penetration of said endoscopic instrument into said adapter;
at least one flange projecting axially from said distal stop means;
a securing means for locking said adapter on to said endoscope; and
characterized in that said adapter carries a deployment assembly activated by actuating means operated from outside the patient by a wire sheath connected to a pusher, wherein said pushing said pusher into said deployment assembly pushes a tissue-affixing clip out of said assembly.

The method of manufacturing the adapter of the invention, its use, and the composition thereof, is not limited except for suitability for use in medical or veterinary procedures. A method of manufacturing an adapter of the invention may be selected from, but is not limited to, one or more of injection molding, insert molding, multi-material molding, casting, mechanical assembly of discrete function components and sub assemblies, bonded assembly of discrete function components and sub assemblies, fused assembly of discrete function components and sub assemblies or any combinations thereof.

Having described the invention in particular embodiments to allow it to be understood by a person of normal in the art, additional embodiments will occur to such a person. The scope of the invention is not limited to the embodiments described, but is limited only by the scope of the claims.

The invention claimed is:

1. An adapter for attaching a device to a distal end of an endoscopic instrument, the adapter comprising:
a distal stop to limit penetration of the endoscopic instrument into the adapter;
at least one flange projecting axially from the distal stop and configured for insertion of the endoscopic instrument therein, the flange comprising a non-closed circumference, the flange having at least one longitudinal opening; and
a securing element releasably attachable to the flange to compress the flange against the endoscopic instrument to secure the adapter to the endoscopic instrument to prevent motion of the adapter with respect to the instrument, the securing element, when attached to the flange, at least partially wrapping around the flange and the instrument therein, and configured to span the opening of the flange;
wherein the flange includes an expandable flange portion defining the opening and a highly expandable membrane portion to accommodate the insertion of an endoscopic device having a diameter greater than that of the distal stop, the membrane portion covering the opening, and the securing element configured to span the membrane portion and the opening.

2. The adapter of claim 1, wherein the distal stop has a closed perimeter.

3. The adapter of claim 1 wherein the flange is comprised of a flexible material to at least partially encircle, with the non-closed circumference of the flange, an endoscopic instrument circumference, the encirclement allowing the securing of the adapter to the distal end of endoscopic instruments having a range of diameters and shapes at their distal tips.

4. The adapter of claim 1, wherein the distal stop has a perimeter with at least one internal protrusion.

5. The adapter of claim 1, wherein the adapter is constructed so that the central axis of said adapter and the center axis of said endoscopic instrument are substantially parallel when said adapter is mounted on said instrument.

6. The adapter of claim 1, wherein the securing element is constructed and arranged to provide a force to impede movement of the adapter with respect to the endoscopic instrument, when the adapter is placed on the endoscopic instrument and the securing element is engaged with the adapter.

7. The adapter of claim 1, wherein the securing element is an elastomeric o-ring.

8. The adapter of claim 1, wherein said at least one flange, after it is secured to the endoscopic instrument, defines at least one region which is open or transparent to allow visualization of tissues surrounding said endoscopic instrument by visualization means mounted on said endoscopic instrument.

9. The adapter of claim 1, further comprising a sheath covering said adapter.

10. The adapter of claim 9 further comprising a sheath or membrane covering the adapter proximally of the distal end of the adapter, which may be deployed before or during a medical procedure.

11. The adapter of claim 10 wherein the sheath is optically clear at least in part.

12. The adapter of claim 11 wherein the sheath is extendable to enclose the full length of the endoscopic instrument.

13. The adapter of claim 1, wherein said adapter is used to attach one or more devices to an endoscopic instrument to allow specific functions to be performed at a tissue site located remotely in the body.

14. The adapter of claim 13 wherein the attached device comprises one or more of a tissue fastener, or a dispenser therefor; additional lumens for access to the operative site; functional means to dynamically resize or reconfigure the attached device portion; drug delivery or medicament dispensing means; energy delivery means; sensor or measurement devices; visualization means; and markers to assist in determination of the location of the endoscope tip.

15. The adapter of claim 13 wherein said at least one device is connected to said adapter by connecting means, wherein said connecting means include without limitation one or more of co-fabrication, mechanical assembly of discrete function components and sub assemblies, bonded assembly of discrete function components and sub assemblies, fused assembly of discrete function components and sub assemblies.

16. The adapter of claim 1, wherein the adapter can accommodate endoscopes varying in diameter over a range wherein the largest diameter of endoscope that can be accommodated by the adapter is at least 150% of the smallest diameter of endoscope onto which the adapter can reliably stabilized.

17. The adapter of claim 1, wherein after the securing of said flange to said endoscopic instrument, a sealing property is created between said adapter and said endoscopic instrument to allow suction to occur at the distal end of said endoscopic instrument upon provision of a vacuum to said endoscopic instrument at its proximal end.

18. The adapter of claim 1, wherein the highly expandable portion is visually clear.

19. The adapter of claim 1, wherein the highly expandable portion overlaps the expandable flange portion.

20. The adapter of claim 1, wherein the opening is a slit.

21. The adapter of claim 1 further comprising at least one delivery channel attached to said adaptor, said channel suitable for the conveyance of at least one of a fluid or an instrument from outside of the body to an interior site.

22. The adapter of claim 21 in which said channel can be changed in functional cross section by one or more of mechanical manipulation and inflation by gas or liquid.

23. The adapter of claim 1, wherein said adapter is used to attach one or more devices to an endoscopic instrument to allow specific functions to be performed at a tissue site located remotely in the body said adaptor comprising:
   a means for attaching a device to said adapter; and
   a means for discharging said device from said adapter.

24. The adapter of claim 1,
   wherein said flange comprises a non closed cross-section portion of a generally hollow cylinder.

25. The adapter of claim 1, further comprising:
   one or more hook-like members for engaging the securing element, the hook-like members located proximal from the distal stop.

26. The adapter of claim 1, wherein the adapter is constructed so that the central axis of the adapter and the central axis of the endoscopic instrument are not concentric when the adapter is mounted on the instrument.

* * * * *